United States Patent [19]

Blough

[11] 4,315,001

[45] Feb. 9, 1982

[54] 2-DEOXY GLUCOSE AS AN ANTIVIRAL AGENT AGAINST HERPES SIMPLEX

[76] Inventor: Herbert A. Blough, 4119 Kottler Dr., Lafayette Hill, Pa. 19444

[21] Appl. No.: 67,504

[22] Filed: Aug. 17, 1979

[51] Int. Cl.$^3$ ............................................. C07H 31/70
[52] U.S. Cl. ........................................ 424/180; 536/1
[58] Field of Search ............................. 536/1; 424/180

[56] References Cited

U.S. PATENT DOCUMENTS 4,000,260 12/1976 Prusoff et al. ......................... 536/23

OTHER PUBLICATIONS

Kilbourne, "Nature," vol. 183, pp. 271–272, 1959.
Ray et al., "The Lancet," Sep. 1974, pp. 680–683.
Goodhart et al., "The New England Journal of Medicine," Jun. 7, 1979, p. 1338.
Blough et al., "Jour. of the American Medical Assn.," Jun. 29, 1979, vol. 241, #26.

*Primary Examiner*—Johnnie R. Brown

[57] ABSTRACT

A method of treating herpes simplex virus by the administration of 2-deoxy-D-glucose is described. The sugar analog is effective in treating genital herpes, labial herpes, and ocular herpes.

7 Claims, No Drawings

2-DEOXY GLUCOSE AS AN ANTIVIRAL AGENT AGAINST HERPES SIMPLEX

The present invention relates to a method of treating herpes simplex virus. In particular, a method is described for the effective treatment of genital herpes, labial herpes and ocular herpes.

Two types of herpes simplex virus (HSV) have been described in the literature. They are generally referred to as type 1 and type 2. The predominant clinical manifestation of type 1 is recurrent herpes labialis (cold sores) and corneal infections (keratitis). Type 2 in humans is primarily associated with recurrent herpetic vulvovaginitis (in women) and penile lesions in men.

Herpes simplex virus, types 1 and 2, account for approximately 500,000 new cases of venereal disease each year, and there are approximately 13 to 15 million sufferers of this disease in the United States alone. Genital herpes simplex infection is characterized by severe pain followed by the appearance of blisters (vesicles) which may coalesce to form large blebes. When the symptoms are allowed to go untreated the virus may then migrate to the deeper tissues of the body such as the lymph nodes and neural tissues resulting in lymphadenopathy, which may be tender, and problems which simulate sciatic nerve neuralgia. In many cases the infection is accompanied by systemic effects such as fever, listlessness, and a "washed-out" feeling. In addition, the virus may spread to the fetus at the time of delivery (causing encephalitis).

Treatment for herpetic infections in other parts of the body, such as the eye, for example, has involved the use of various nucleoside derivatives such as adenine arabinoside and trifluoromethylthymidine. Treatment of genital lesions has involved the use of dyes and photodynamic inactivation. Smallpox vaccine, BCG (Bacillus Calmette-Guérin) and influenza virus vaccine have been used intradermally in the treatment of genital herpes but none of the known methods has proved to be satisfactory in treating the disease.

It has now been determined that the glucose analog 2-deoxy-D-glucose is effective as a chemotherapeutic agent in the treatment of herpes keratitis and herpes uveitis and it also has unique efficacy in the treatment of genital herpes infections. 2-Deoxy-D-glucose is a simple sugar molecule which is found in many lower organisms. It can be obtained from plants and other eukaryotic cells. It is colorless and stable in aqueous solutions.

The present invention, therefore, provides a safe and convenient method of treating genital herpes, labial herpes and herpes keratitis with uveitis.

DESCRIPTION OF PREFERRED EMBODIMENTS

The approach to the treatment of genital and labial herpes virus infections has, in general, been restricted to the use of those agents that inhibit synthesis of or interact with viral nucleic acids, namely, 5-iodo-2'-deoxyuridine, 9-$\beta$-D-arabinofuranosyladenine, and 5-trifluoromethyl-2'-deoxyuridine, as well as photodynamic inactivation using intercalating agents such as acriflavine or proflavine followed by white (visible) light. All these compounds have been proved to be totally ineffective in the treatment of genital herpes and herpes uveitis. Many of the antiviral drugs interfere with DNA metabolism and are potential mutagens; alternatively, persons may be sensitized with the emergence of a resistant population of virions. 2-Deoxy-D-glucose is a relatively non-toxic compound that is administered in a simple fashion and penetrates rapidly into most tissues, depending upon the vehicle employed.

The antiviral action of 2-deoxy-D-glucose has been known for 20 years, however, its clinical use has not been explored. The metabolism of 2-deoxy-D-glucose has been reviewed. 2-Deoxy-D-glucose is incorporated directly into glycoproteins and glycolipids and appears to block the cellular synthesis of the major glycosylated polypeptide of HSV. In HSV-infected cells treated with 2-deoxy-D-glucose, hematosides are notably reduced, with an accumulation of precursor molecules, namely, the ceramide backbone. In addition, 2-deoxy-D-glucose appears to prevent the synthesis and transport of non-structural glycolipids. 2-Deoxy-D-glucose, therefore, is a rational and effective chemotherapeutic agent in the treatment of genital herpes because of its ability to prevent the synthesis of macromolecules required for envelope biogenesis and recognition phenomenon.

Although 2-deoxy-D-glucose shows a unique efficacy in the treatment of genital herpes, it has also been found to be effective for the treatment of labial or oral herpes as well as ocular herpes.

For use in treating herpetic lesions, 2-deoxy-D-glucose is formulated in a pharmaceutically acceptable, non-irritating vehicle. The vehicle may be in any suitable form such as a lotion, cream, oil or emulsion or it may be formulated into a rectal or urethral suppository. Suitable pharmaceutically acceptable vehicles include polyethylene glycol, mineral oil, petrolatum, propylene glycol, glycerol, and the like or a buffered acid jelly. The sugar analogue may be used alone or in conjunction with a fungicide such as miconazole nitrate, miconazole or mylostatin. The fungicide serves as a control of fungal growth. The formulated sugar is then applied topically or intravaginally to the infected area and treatment is continued until the lesion is healed. The amount of 2-deoxy-D-glucose employed in the formulation is generally between 10 mmole and 125 mmole per day in divided doses. The preferred range is 12 mmole to 50 mmole. When used in the form of a suppository, the suppository is compounded with about 3 mg to 10 mg of 2-deoxy-D-glucose. For labial or oral herpes about 10 mmole to 25 mmole of 2-deoxy-D-glucose is used (per day).

The invention may be illustrated as follows: Thirty-six women with genital herpes infections (proved by virological or cytological means) were treated in a double-blind placebo-controlled study with 2-deoxy-D-glucose for a three-week period. Of the cases reported in this series, 10% were type 1, and 90% were type 2. Tissue culture was positive for HSV in all cases (both placebo- and 2-deoxy-D-glucose-treated cases) except one; in the latter, diagnosis was made by cytological examination. Sixty-five percent of all women, either placebo or 2-deoxy-D-glucose treated, had concomitant positive cervical cultures. Colposcopy followed by cytological examination, namely, examination for giant cells, was positive in 10% of all cases. The following five mixed infections were encountered: two with *Trichomonas vaginalis;* two with *Candidia albicans,* and one patient with HSV and both trichomonas and monilial infections. Gonorrhea and syphilis were not seen in this group. Herpesvirus serological examination offered little to the diagnostic regimen except in those cases where an anamnestic response was encountered.

Patients with initial infections treated with 2-deoxy-D-glucose had a rapid relief of pain and dysuria (the two most common complaints occurring in 100% and 70%, respectively) within 12 to 72 hours vs. eight to ten days in those receiving placebo treatment. Therapy with 2-deoxy-D-glucose substantially decreased the duration of lesions after initiation of therapy (Table 1). With initial mucocutaneous cases, both the lesions and subjective symptoms persisted 60% longer in the placebo-treated controls than in the 2-deoxy-D-glucose-treated patients. In placebo-treated cases, the number of lesions frequently remained the same or increased, and in a few of these, they progressed to extensive coalescent or excoriating lesions that involved the entire anogenital region as well as tender lymphadenopathy. In contrast, those patients successfully treated with 2-deoxy-D-glucose had a more rapid devolution of symptoms and progressive lesions were not observed. In 2-deoxy-D-glucose-treated initial patients, lesions became negative for HSV within four days compared with 15 days for placebo-treated controls (Table 1); the earliest negative culture following 2-deoxy-D-glucose treatment was 24 hours.

In the case of recurrent infections, response was immediate after the institution of 2-deoxy-D-glucose. The duration of the lesions following therapy in this group was approximately half of that observed in placebo-treated patients ($P<0.001$), and virus shedding was reduced (Table 1). The clinical course of placebo-treated controls was the same as that of the untreated population (with recurrent genital herpes). Deoxyglucose treatment reduced or prevented recurrence in both initial and recurrent cases (Table 2). During a two-year period, among all patients with initial HSV treated with 2-deoxy-D-glucose, there were two recurrences. The recurrence rate averaged 35% to 40% in this study as well as in a subselected population of eight patients with initial disease treated with miconazole only. Among the 2-deoxy-D-glucose-treated patients with recurrent infections, eight patients had no recurrence, eight had fewer exacerbations, and the remaining two failed to respond to therapy. The latter two patients had been previously treated by photodynamic inactivation. No resistant strains emerged during the course of 2-deoxy-D-glucose therapy. and no untoward reactions to 2-deoxy-D-glucose were encountered.

TABLE 1

Effect of 2-Deoxy-D-Glucose on Genital Herpesvirus Infection*

| Therapy Used | Duration of Lesion Following Therapy, Days** | Duration of Positive Viral Culture Following Treatment, Day** |
|---|---|---|
| Initial | | |
| Placebo | 18.0 ± 3.00 | 15.3 ± 2.52 |
| 2-Deoxy-D-glucose | 8.2 ± 0.90 | 4.3 ± 0.53 |
| P | <.001 | <.001 |
| Recurrent | | |
| Placebo | 12.0 ± 1.00 | 15.3 ± 2.50 |
| 2-Deoxy-D-glucose | 6.8 ± 0.6 | 4.4 ± 0.46 |
| P | <.001 | <.001 |

*Patients were treated topically with 2-deoxy-D-glucose in a vehicle or with a placebo (vehicle alone or vehicle plus D-glucose).
**Number of days ± SEM.

TABLE 2

Efficacy of 2-Deoxy-D-Glucose vs Placebo Therapy on Recurrence of Genital Herpes

| Therapeutic Regimen | No Recurrence, % | Decreased Frequency of Recurrences, % | Unfavorable Response Based on Recurrent Rate, %* |
|---|---|---|---|
| Initial | | | |
| Without 2-deoxy-D-glucose (n = 8)** | 65 | Not Applicable | 31 |
| With 2-deoxy-D-glucose (n = 18)*** | 89 | Not Applicable | 11 |
| P | <.001 | — | — |
| Recurrent Disease**** | | | |
| Without 2-deoxy-D-glucose (n = 7)** | 0 | 0 | 100 |
| With 2-deoxy-D-glucose (n = 18)*** | 45 | 45 | 10 |

*A 10% rate for recurrent disease with 2-deoxy-D-glucose refers to no change in either severity or frequency.
**Patients treated with vehicle alone or vehicle plus D-glucose.
***Patients treated with 2-deoxy-D-glucose.
****For recurrent disease in 90% of the patients with a favorable Response P<.001.

For labial herpes, the treatment consisted of the application of 2 to 3 drops of a 50 millimolar solution of 2-deoxy-D-glucose in sterile anhydrous glycerol. Lesions epitheliazed in 4–5 days with complete healing within a week. Symptoms of pain, salivation, and swelling abated in 48 hours.

For ocular herpes, the treatment consisted of the application of 2 to 3 drops of a 20 or 50 millimolar solution of 2-deoxy-D-glucose in sterile anhydrous glycerol applied every three hours during the waking period. Difficult lesions such as herpetic ulcers at the limbus epitheliazed in four days. Vision frequently 20/100–20/200, returned to normal levels within five days. Herpetic uveitis responded equally as well to the treatment with 2-deoxy-D-glucose.

The following are examples of formulations containing 2-deoxy-D-glucose:

A. Miconazole Nitrate Cream with 2-Deoxy-D-Glucose
Procedure for 3000 g
    1. Add the 2-Deoxy-D-Glucose to a portion of the formula Purified Water and mix until solution is effected.
        2-Deoxy-D-Glucose        5.25 g
    2. Place the MONISTAT-7 Cream into a stainless steel mixing bowl.
        MONISTAT-7        2970.0 g
    3. Slowly add the 2-Deoxy-D-Glucose solution to the cream in the mixing bowl.
    4. Rinse the vessel containing the solution of 2-Deoxy-D-Glucose with the remainder of the formula Purified Water and add to the cream in the mixing bowl. Mix until uniform using a planetary mixer. The total amount of Purified Water used is 24.75 g.

B. Cream with 2-Deoxy-D-Glucose
Procedure for 3000 g
1. Add the 2-Deoxy-D-Glucose to a portion of the formula Purified Water and mix until solution is effected.

2-Deoxy-D-Glucose          5.25 g

2. Place the Placebo Cream Vehicle into a stainless steel mixing bowl.

Placebo Cream Vehicle      2970.0 g

3. Slowly add the 2-Deoxy-D-Glucose solution to the cream in the mixing bowl.
4. Rinse the vessel containing the solution of 2-Deoxy-D-Glucose with the remainder of the formula Purified Water and add to the cream in the mixing bowl. Mix until uniform using a planetary mixer. The total amount of Purified Water used is 24.75 g.

C. Placebo Cream
Procedure for 3000 g
Place the following into a stainless steel vessel.

Placebo Cream Vehicle      2970.0 g
   Purified Water, USP          30.0 g

Mix until uniform using a planetary mixer.

D. Alternative Method of Preparing Monistat Formulation
One milliliter of a 500 mM aqueous solution of 2-deoxy-D-glucose is added to 47 gm of a base consisting of
- mineral oil
- pagoxal 7-stearate
- peglicol 5-oleate
- butylated hydroxyanisole
- benzoic acid and water In addition, special suppositories made of the monistat vehicle in which is compounded 3 mg of 2-deoxy-D-glucose can be made in one of two ways. Either the 2-deoxy-D-glucose can be made prior to the hardening of the suppository into solidified state or alternatively the suppositories can be drilled and filled with a cream containing monistat vehicle in the equivalent of 3 mg of 2-deoxy-D-glucose. In all cases these are weighed and ascertained for biological activity and for the presence of the active ingredient by gas liquid or thin layer chromotography.

I claim:

1. A method for treating herpes simplex virus infections in a human patient which comprises treating said patient with a composition comprising an amount of 2-Deoxy-D-Glucose which is effective against ocular herpes, labial herpes or genital herpes, in a pharmaceutically acceptable carrier.

2. The method of claim 1 wherein the amount of 2-deoxy-D-glucose is between 10 mmole and 125 mmole.

3. The method of claim 1 wherein the patient is treated by topically applying the 2-Deoxy-D-Glucose to the affected area.

4. The method of claim 1 wherein the patient is treated intravaginally.

5. The method of claim 4 wherein an antifungal agent is additionally present.

6. The method of claim 5 wherein the antifungal agent is miconazole nitrate.

7. The method of claim 1 wherein the patient is treated rectally.

* * * * *